United States Patent
Rudolph

(10) Patent No.: US 6,528,790 B2
(45) Date of Patent: Mar. 4, 2003

(54) METHOD AND APPARATUS FOR DETECTING WATER ON A SURFACE OF AN OBJECT

(75) Inventor: Ralph G. Rudolph, Center Valley, PA (US)

(73) Assignee: Bethlehem Steel Corporation ( * ) Notice: Subject to any disclaimer, the term of this patent is extended or adjusted under 35 U.S.C. 154(b) by 28 days.

(21) Appl. No.: 09/847,896

(22) Filed: May 3, 2001

(65) Prior Publication Data
US 2002/0162962 A1 Nov. 7, 2002

(51) Int. Cl.$^7$ ................................................ G01N 21/86
(52) U.S. Cl. ................................ 250/339.1; 250/341.1; 250/341.8
(58) Field of Search ..................... 250/339.1, 341.1, 250/341.8, 559.5; 356/429, 430, 431

(56) References Cited

U.S. PATENT DOCUMENTS

| | | | |
|---|---|---|---|
| 3,734,628 A | | 5/1973 | Michishita et al. |
| 3,825,351 A | | 7/1974 | Seki et al. |
| 4,005,926 A | | 2/1977 | Manktelow et al. |
| 4,378,755 A | * | 4/1983 | Magnusson et al. ........ 118/684 |
| 4,591,271 A | | 5/1986 | Byers |
| 4,748,329 A | * | 5/1988 | Cielo et al. .................. 250/560 |
| 5,218,206 A | * | 6/1993 | Schmitt et al. .............. 250/339 |
| 5,226,107 A | * | 7/1993 | Stern et al. .................. 392/416 |
| 5,313,202 A | * | 5/1994 | Hansman et al. ........... 340/962 |
| 5,319,975 A | | 6/1994 | Pederson |
| 5,483,346 A | | 1/1996 | Butzer |
| 5,684,296 A | | 11/1997 | Hamblin et al. |
| 5,761,999 A | | 6/1998 | Lippold et al. |
| 5,796,344 A | * | 8/1998 | Mann et al. ................. 340/583 |
| 5,808,734 A | | 9/1998 | Kolari |
| 5,835,220 A | | 11/1998 | Kazama et al. |
| 5,929,996 A | | 7/1999 | Itagaki et al. |
| 6,052,056 A | * | 4/2000 | Burns et al. ................. 340/583 |

* cited by examiner

Primary Examiner—Constantine Hannaher
Assistant Examiner—Tim Moran
(74) Attorney, Agent, or Firm—Harold I. Masteller, Jr.

(57) ABSTRACT

A method and apparatus for detecting and removing water from a surface of a moving metal sheet in continuous treatment line to prevent the formation of water stains thereon. A selected surface area of the moving metal sheet is illuminated with infrared radiation having a wavelength substantially absorbed by water, and an optical sensor system is employed to view images reflected off the selected surface area. An optical bandpass filter limits transmission of infrared light to within a specific range of wavelengths known to be strongly absorbed by water. The sensor assembly produces a signal representative of the intensity of the reflected light. If the intensity signal is lower than a predetermined level, water is detected and the signal may be used to trigger a control device that sounds alarms, records the event, or otherwise controls the environment of the object so that detected water may be removed to prevent the formation of water stains. The present invention is particularly suited for detecting the presence of water on a moving steel sheet treated in a continuous coating line.

43 Claims, 4 Drawing Sheets

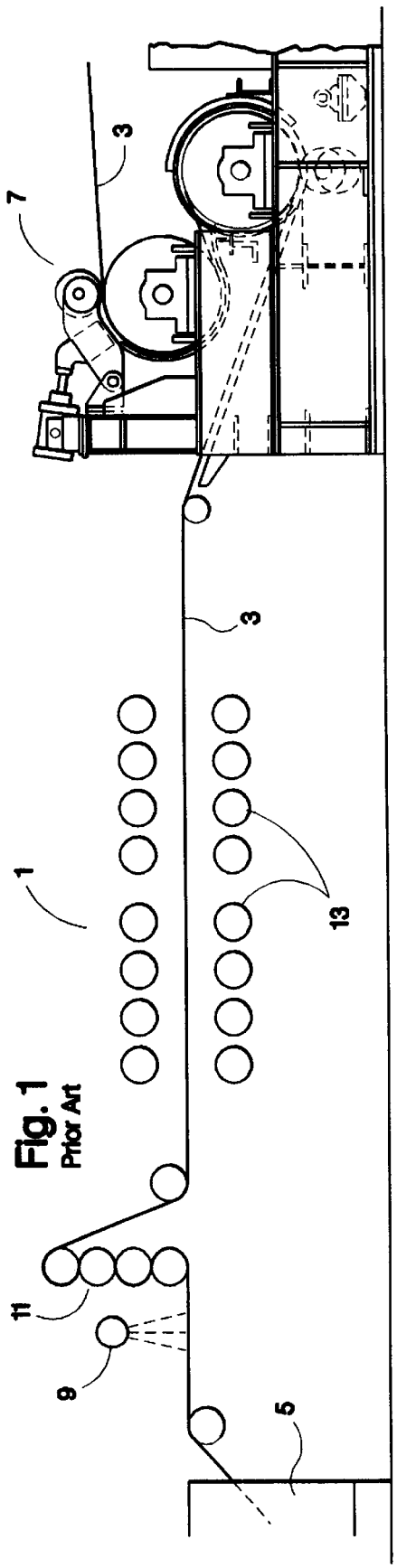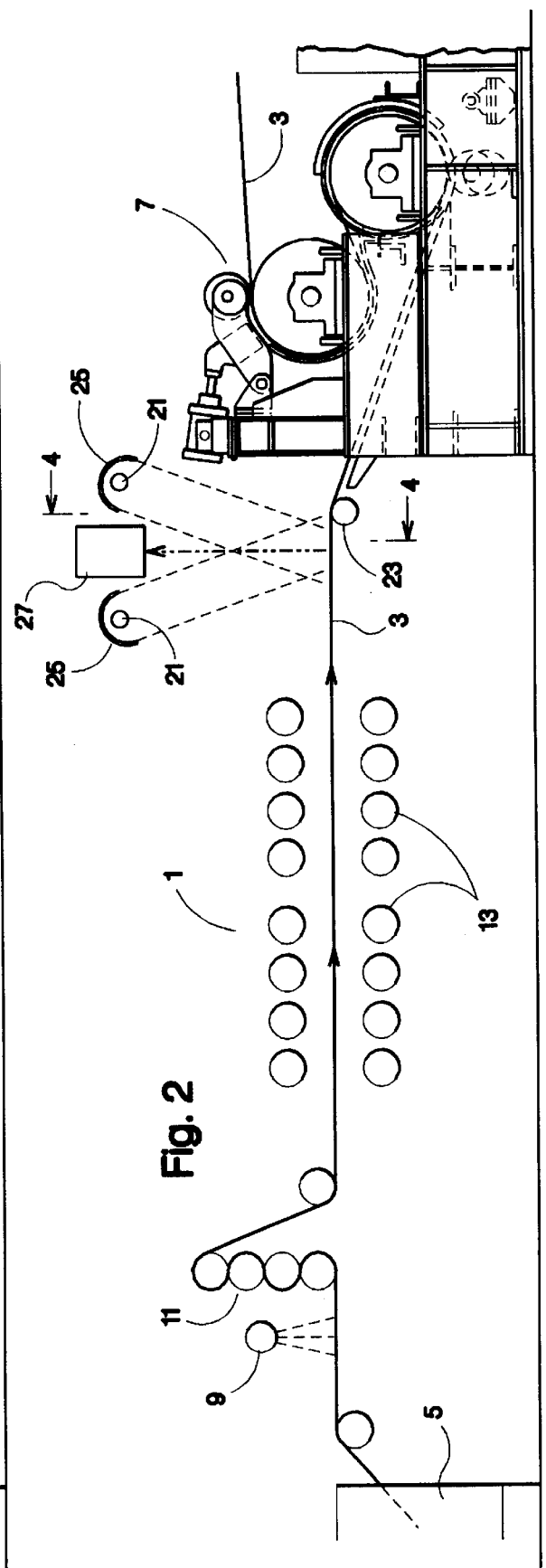

METHOD AND APPARATUS FOR DETECTING WATER ON A SURFACE OF AN OBJECT

FIELD OF THE INVENTION

The present invention is directed to a method and apparatus for detecting and removing water from the surface of an object, and more particularly, it is directed to the use of radiant energy, for example infrared light, to detect and remove water from the surface of a moving metal sheet processed in a continuous treatment line to prevent the formation of water stains thereon.

BACKGROUND OF THE INVENTION

Within the steel industry, many different types of steel strips are produced, often with various coatings ranging from other metals such as for example, tin, zinc, and zinc alloy, to organic protective layers. The different processing steps involved in manufacturing such a variety of different coated steel sheet products requires the strip to be uncoiled and recoiled many times. The uncoiled strip is often deliberately exposed to water or water containing components during the manufacturing process. If water accidentally remains on the strip when it is recoiled, the remaining water will cause various types of oxides to form within the coil windings, the formed oxides reducing product quality and sometimes ruining the entire steel sheet coil. Therefore, the presence of water must be avoided in coiled steel sheet product because the presence of water will lead to product loss at a considerable cost to the manufacturer.

FIG. 1, labeled Prior Art, shows the rinse section 1 of a typical continuous coating line. The steel sheet 3 is shown exiting a scrubber tank 5, moving through hot air dryers 1 & 13, and entering a coiler 7 where the steel sheet product is coiled for further processing or packaged for customer shipping. In a high speed coating line, the steel sheet product 3 travels at speeds of up to 3000 feet per minute. The fast moving sheet exits the scrubber tank 5, is sprayed with an oil/water emulsion at sprayer 9, and the strip passes through a set of wringer rollers 11 where excess water is "squeezed off" or removed from the product surface. To further insure that all water is removed from the steel sheet surface, the sheet product 3 passes between a plurality of hot air dryers 1 & 13 before reaching tension bridle rolls 7 of the coiler. At the higher speeds encountered in modem coating lines, the wringer rolls 11 are less effective at removing excess water from the product surface. As a result, there is a vary real possibility of having water present on the steel sheet surface when the strip 3 enters coiler (not shown).

State-of-the-art systems employed to remove the water occasionally fail to operate properly resulting in inferior product. Thus, it is desirable to have a system that automatically and non-invasively detects the presence of water on the moving steel sheet or strip 3, which heretofore has been void in the art. Previously, the only known method of detecting water was to manually hold a tissue or other water absorbent material on the surface of the steel sheet as it moved toward the coiler, and visually inspect the tissue for evidence of moisture. However, such a method is dangerous, inconsistent, and impractical.

It is known in the prior art to detect defects on a moving body such as a cold rolled strip. U.S. Pat. No. 3,734,628 discloses a method and apparatus for detecting defects in strip product, and the U.S. Pat. No. 3,734,628 is incorporated herein by reference. The '628 reference teaches coating the strip with a film of oil, and the apparatus scans the surface with infrared light, having a specified wavelength range capable of penetrating the oil to detect underlying defects. However, such a method and apparatus for detecting defects is not suited for detecting the presence of water on a steel sheet surface moving at high speed.

U.S. Pat. No. 5,684,296 discloses using infrared light to detect the presence of a liquid, and the U.S. Pat. No. 5,684,296 is hereby incorporated herein by reference. However, this application is incompatible with the use of electronic sensors and requires the optical device to come into contact with the liquid. Therefore, the 296 patent does not have practical application as a non-invasive system for the detection of water, and in particular, for the detection of water on a continuous moving metal sheet.

Additional methods and apparatus to detect water in other environments are also known in the art. However, these prior art applications have no practical application for detecting water on a surface of an object as in the present invention.

Generic methods and apparatus to scan objects with infrared light or other light are well known in the art and are disclosed in various forms in the following references, U.S. Pat. Nos. 5,929,996; 5,835,220; 5,761,999; 4,005,926; and 3,825,351, all of which are incorporated herein by reference.

Therefore, as clearly illustrated above, there is a long felt need within the industry to provide a non-invasive method and apparatus for detecting the presence of water on a surface of an object, and particular, there is a long felt need to provide a method and apparatus capable of detecting the presence of water on the surface of a continuous steel sheet moving at a high speed in a manufacturing operation.

SUMMARY OF THE INVENTION

The present invention is directed to a method and apparatus for detecting the presence of water on a surface of an object using radiation. A surface area to be detected is illuminated with radiation having a wavelength substantially absorbed by water. An optical system is employed to view images reflected from the surface area. A bandpass filter is disposed between the surface area being monitored and the sensor to limit transmission of radiation to within a specific range of wavelengths known to be strongly absorbed by water. Thus, areas having no water will appear brightly illuminated and the reflected radiation more intense and areas where water is present will appear dark, the reflected radiation being less intense. The sensor assembly produces a signal representative of the intensity of the reflected radiation. If the intensity signal is lower than a predetermined level, water is detected and the signal may be used to trigger alarms or otherwise control the environment of the object. The present invention is particularly suited for detecting the presence of water on a moving strip of metal during a manufacturing process.

BRIEF DESCRIPTION OF THE DRAWINGS

The above and other objects and advantages and novel features of the present invention will become apparent from the following detailed description of the preferred embodiment of the invention illustrated in the accompanying drawings, wherein:

FIG. 1 (Prior Art) is a schematic view showing the rinse section in a continuous coating line.

FIG. 2 is similar to FIG. 1 and shows one embodiment of the water detection apparatus of the present invention.

DETAILED DESCRIPTION OF THE PREFERRED EMBODIMENT

Figure 3:
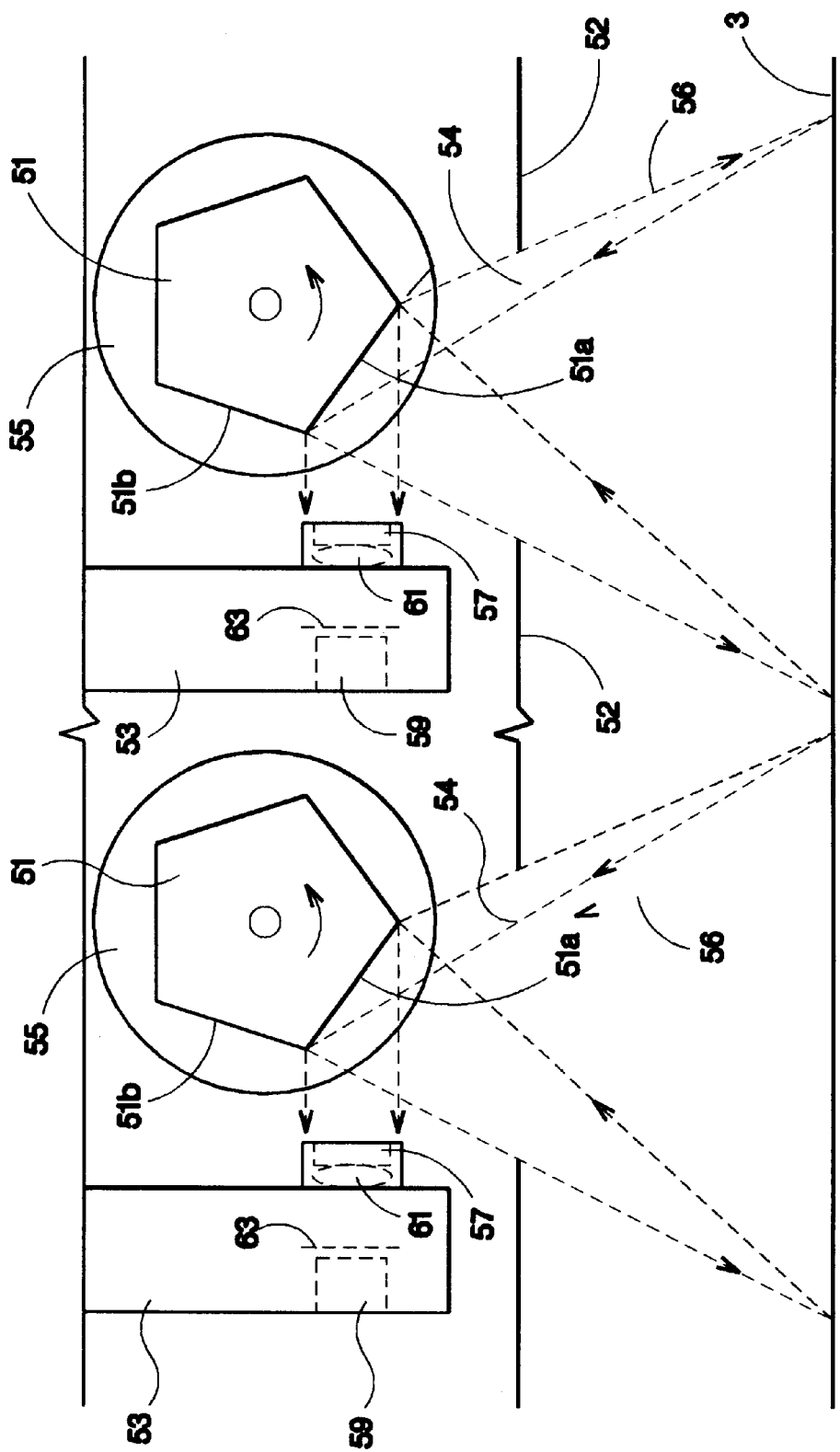
FIG. 3 is a view showing scanner assemblies employed to sense reflected light.

The present invention is directed to sensing the presence of water on the surface of an object by using reflected radiation, for example, light. In the preferred embodiment, the presence of water is detected by using reflected infrared light because infrared light has a wavelength substantially absorbed by water. However, it should be understood, that other energy sources and wavelengths that are similarly absorbed by water may be used to detect water without departing from the scope of this invention. The infrared light is directed onto the strip, and if water is present, a substantial amount of the infrared light will be absorbed. Consequently, the intensity of the infrared light reflected from the strip surface will be less than the irradiated infrared light. A "substantial amount" of infrared red light absorbed by water simply means that a sufficient amount of light is absorbed by the water to detect a noticeable change in the intensity between the irradiated and reflected light.

Infrared light of different wavelengths has different transmittance and absorption rates through different mediums. For water, there are several strong absorption bands. Specifically, wavelength bands within a range from 1–2 microns, 2.5–3.5 microns and 6–7 microns are strongly absorbed by water. Therefore, infrared light having wavelengths within the cited ranges will have a reduced intensity after reflection through water. It has been demonstrated that infrared light having a wavelength in a range from 2.7–2.9 microns is particularly suited to detect the presence of water and is the preferred wavelength range for detecting water according to the present invention.

The method of the present invention includes providing an infrared light source having a wavelength that is substantially absorbed by water, the infrared light being irradiated/directed onto a surface of the object being monitored for the presence of water. The infrared light is reflected off the surface is of the object and sensed. A signal is produced representative of reflected light intensity and compared to the irradiated/directed light intensity. If the reflected light intensity is less than the irradiated/directed light intensity by a predetermined amount, a presence of water is detected. If the reflected light intensity is substantially, for example, equal to or about the same as the directed/irradiated light intensity, no water is detected. The following apparatus, that also forms part of the present invention, provides means for carrying out the steps of the aforementioned method for detecting the presence of water on the surface of a moving object.

FIG. 2 represents a steel sheet or strip 3 in a continuous high speed manufacturing line similar to the prior art described in FIG. 1, and a mechanism to automatically and non-invasively detect the presence of water on the steel sheet 3. An energy source, and in particular, an infrared light source 21, such as a quartz infrared heater, is positioned above a stabilized, for example, not fluttering portion of the strip proximate a roller 23 supporting a direction change in the conveyed strip 3. In the preferred embodiment, a pair of longitudinally extending infrared heaters 21, each having a parabolic reflector 25, extend across the width of strip 3 so that the strip is sufficiently illuminate across its width. It is to be understood that one of ordinary skill in the art can employ other sources of infrared light within the pre-described wavelength range or other wavelength ranges, the details of which need not be further discussed.

A sensor assembly 27 is positioned to receive light reflected from the surface area being monitored for the presence of water. In the preferred embodiment shown in FIG. 2, sensor assembly 27 is positioned between the infrared illuminators 21 and is disposed above the strip 3 to sense infrared light reflected off the surface of the steel sheet 3. As the steel sheet 3 is conveyed beneath sensor assembly 27, the entire width of the strip 3 is continuously illuminated by the infrared light source 21. The sensor assembly 27 is adapted to sense light that is reflected across a width portion of the conveyed sheet 3. Therefore, the system facilitates continuous monitoring to detect water on the entire surface area of the continuous moving sheet 3. The sensor assembly 27 may be integrated with a computer system or other control device (not shown) for further processing or control to initiate an alarm, mark portions of the sheet where water is detected, control the speed of the conveyed strip 3, record the frequency of water detection or even shut down strip movement. Other events are also contemplated by the present invention.

FIG. 3 represents one embodiment of the sensor assembly according to the present invention. In the present embodiment, the surface of the steel sheet 3 is scanned with polyhedral rotating mirrors 51 that receive and direct reflected light into a detector box 53. As the polyhedral mirror 51 rotates, each side or mirror surface will scan a portion of the strip width. Depending on the sheet in combination with the window size or scan width covered by a scanning mirror 51, a plurality of rotating scanning mirrors 51 may be needed to scan the full sheet width. FIG. 3 depicts two such rotating polyhedral mirrors 51 driven by a motor 55 in coordination with the moving sheet 3. The relationship of the lateral scanning of the rotating mirrors 51 and displacement of the strip 3 will cause each side 51a of each mirror 51 to scan an angled portion of the strip 3. As each mirror 51 rotates exposing a subsequent side 51b, an immediately adjacent parallel portion of the strip 3 is sensed. Thus, the entire length, as well as the width, of the moving steel sheet 3 is continuously scanned. The plurality of scanning mirrors 51 is arranged to slightly overlap a scan area to ensure that the entire width of the strip 3 is scanned. A screen 52 having openings or windows 54 may also be employed to limit the amount of reflected light reaching each scanning mirror 51. Depending on the overall sheet, any number of scanning mirrors may be used to cover the fill sheet width. In the present embodiment, only two scanning mirrors are shown being used to scan the full width of sheet 3, each scanning mirror 51 being attached to a motor and rotated at a speed of 3000 rpm. The combination of a five-sided polyhedral mirror rotated at 3000 rpm results in a scanning rate of 15000 scans per minute. The scanning mirrors receive and redirect reflected light from the sheet surface and onto a sensor 59 housed within detector box 53. It is to be understood, however, that one of ordinary skill in the art may change the rotational speed and arrangement of the scanning mirrors 51 in response to the size and speed of a moving strip 3 so that the entire surface of a particular moving strip 3 is scanned and monitored to detect the presence of water.

Figure 5:
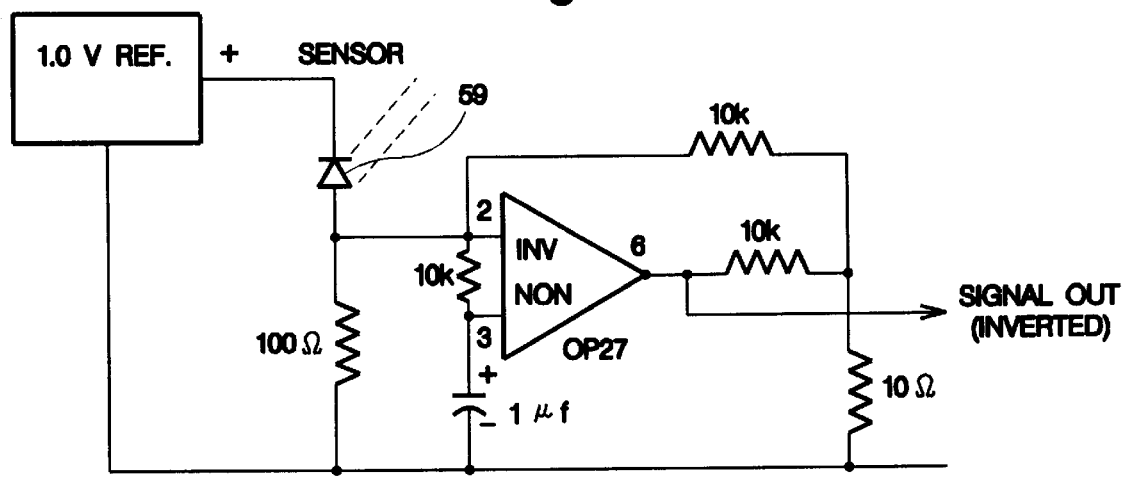
FIG. 5 is a circuit diagram of a high band pass filter amplifier.
Figure 6:
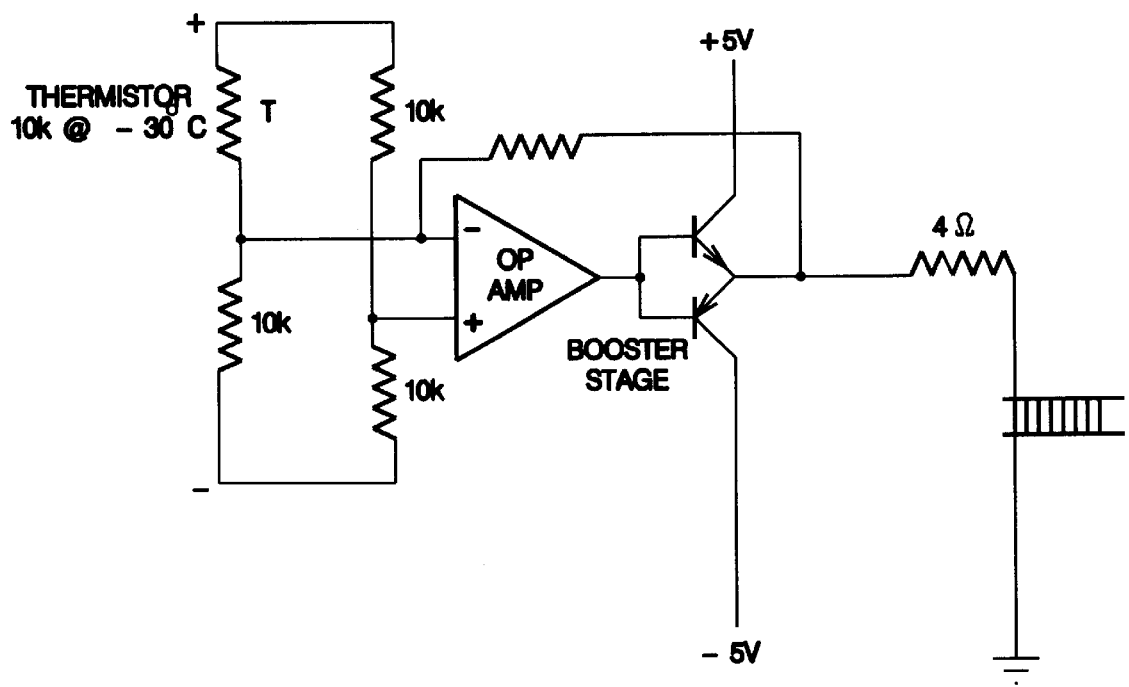
FIG. 6 is a closed loop circuit diagram of a thermoelectrically cooled sensor.

The detector box 53 includes a band pass filter 57 that selectively limits the light falling on sensor 59 to a pre-described wavelength range. As previously mentioned the preferred range of wavelengths is from 2.7–2.9 microns. A lens 61, such as, for example but not limited to, an adjustable focus calcium fluoride lens, is employed in conjunction with a pinhole stop 63 to focus the reflected light onto the sensor 59. An exemplary thermoelectrically cooled sensor such as the J12 series of Indium Arsenide photovoltaic infrared diodes produced by Judson Technologies, may be used to receive and convert the reflected light or radiation 56 to an electrical signal, the output signal being responsive to the reflected light intensity. An amplifying circuit, such as the exemplary circuit shown in FIG. 5, amplifies and converts the output signal from sensor 59 to a voltage signal suitable for communication with a computer or other control device. Sensor 59 is also preferably cooled as indicated in the circuit shown in FIG. 6.

Figure 4:
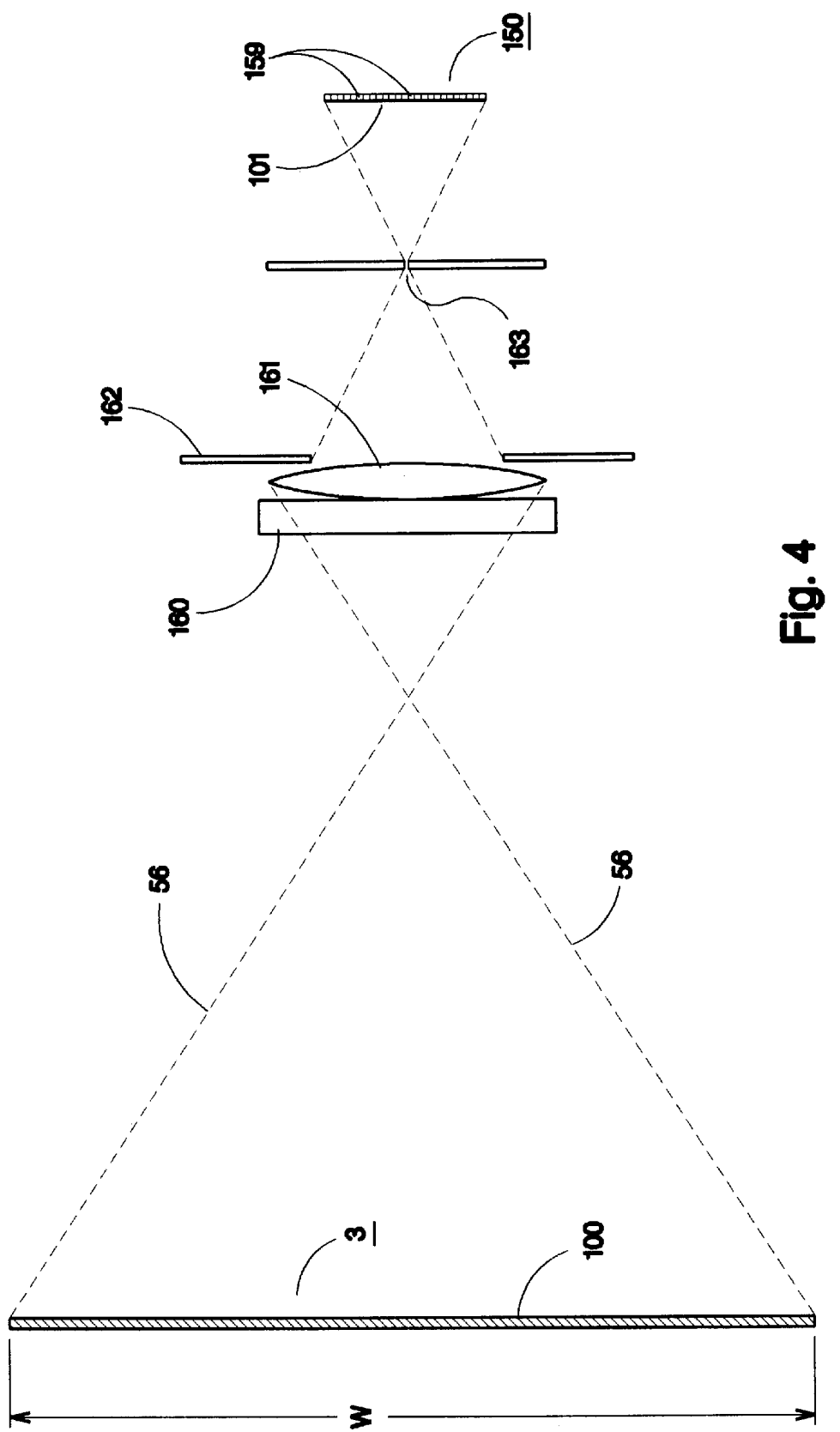
FIG. 4 a view taken along the lines 4—4 of FIG. 2 showing an array of detectors to sense light reflected from the steel sheet surface.

Referring to FIG. 4 showing an alternate embodiment of the present invention, instead of using rotating mirrors 51 to scan a target surface area, a linear array 150 of sensors 159 is arranged to receive radiation reflected from a target surface area 100 that extends across the entire width W of the sheet 3. An image 101 of the target surface area is projected onto the linear array of sensors 159 using a suitable optical system known to one skilled in the art. Depending on the size of width W, and depending on the window area of each sensor 159 within array 150, the number of sensors within an array will vary in order to monitor the entire sheet width. As in the previous embodiment, sensors 159 will receive reflected radiation through an optical system having an associated filter 160 to limit the transmission of light to a selected wavelength, and an optical lens 161, stop 162 and pinhole aperture 163 arrangement capable of focusing the reflected light image 101 onto the linear array 150 and a filter (not shown) to limit the transmission of infrared light to within the aforementioned pre-described wavelength ranges.

It should be understood that FIG. 4 is a schematic representation of the alternate embodiment as a detailed depiction of each of the many sensors and corresponding filters and optical lens is not practical. It is also to be understood that one of ordinary skill in the art can arrange an array 150 of sensors 159 to view or monitor the entire width W of the strip. For example, if a 30 inch wide steel sheet is being monitored to detect the presence of water, a suitable linear array should comprise 64 elements with each sensing element connected to an amplifying circuit in combination with an associated optical system including a filter and lens. Of course, two or more sensor arrays and optical systems may be used to improve image resolution without departing from the scope of this invention.

While the foregoing invention has been shown and described with reference to a preferred embodiment, it will be understood by those possessing skill in the art that various changes and modifications may be made without departing from the spirit and scope of the invention.

I claim:

1. An apparatus for non-invasive detection of water on a surface of a steel sheet coated in a continuous coating line to prevent the formation of water stains thereon, said apparatus comprising:
   a) an infrared light source positioned to transmit a generated infrared light of a predetermined intensity onto a selected surface area of the steel sheet, said generated infrared light having a wavelength substantially absorbed by water;
   b) a sensor assembly having a sensor positioned to sense reflected infrared light reflected off said selected surface area, said assembly producing a signal representative of a second intensity of said reflected infrared light for comparison with said predetermined intensity to thereby detect a presence of water on said selected surface area; and
   c) a control device to initiate a condition whereby detected water is removed from the surface of the steel sheet before coiling to prevent the formation of water stains thereon.

2. The invention according to claim 1, further comprising:
   a) a filter located between said infrared light source and said sensor to limit an amount of said reflected infrared light detected by said sensor within a predetermined wavelength range.

3. The invention according to claim 2, wherein said filter is disposed proximate said sensor and between said select area of said object and said sensor.

4. The invention according to claim 2, wherein said filter limits transmission of infrared light having a wavelength in a range from 2.5 to 3.5 microns.

5. The invention according to claim 2, wherein said filter limits transmission of infrared light having a wavelength in a range from 2.7 to 2.9 microns.

6. The invention according to claim 2, wherein said filter limits transmission of infrared light having a wavelength in a range from 6–7 microns.

7. The invention according to claim 2, wherein said filter limits transmission of infrared light having a wavelength in a range from 1–2 microns.

8. The invention according to claim 2, wherein said sensor is an indium arsenide photovoltaic infrared diode sensitive to infrared wavelengths within a range from 1 to 3.5 microns.

9. The invention according to claim 2, in combination with a rinse section of a steel treatment assembly, wherein said object is a moving sheet of steel conveyed along said rinse section between a drying stage area and a coiler stage of said steel treatment assembly, said infrared light source and said sensor assembly being positioned proximate a roller supporting a turn in said conveyed strip.

10. According to claim 9, wherein said sensor assembly includes a plurality of sensors, said apparatus further comprising:
   a) a plurality of rotating polyhedral mirrors disposed between said strip and said sensor assembly and each positioned to scan a portion of an entire width of said strip and direct infrared light reflected off said portion of said strip toward a corresponding one of said plurality of sensors thereby facilitating sensing of said entire width of said strip.

11. The apparatus according to claim 9, wherein said sensor assembly comprises an array of sensors, each of said sensors adapted to sense a width portion of said strip, said array of sensors together sense reflected light across an entire width of said strip.

12. The invention according to claim 2, wherein said light source comprises a pair of quartz infrared heaters disposed above said object and each having a parabolic reflector mounted there above to illuminate said select area by infrared radiation.

13. The apparatus according to claim 1, wherein said object is opaque substantially preventing said infrared light from passing through said surface.

14. The invention according to claim 2, wherein said filter limits transmission of infrared light having a wavelength between 1.0 to 2.7 microns and a wavelength between 3.2 to 3.5 microns.

15. An apparatus for non-invasive detection of water on a strip of steel in combination with a rinse section of a steel treatment facility, said strip of steel being conveyed along said rinse section between a drying stage area and a coiler, said apparatus comprising:
   a) a detection assembly provided to detect a presence of water on said strip and positioned along said rinse section between said drying stage area and said coiler proximate a roller supporting a turn in said conveyed strip, said detection assembly including;
   b) an infrared light source including a pair of quartz infrared heaters disposed above said strip, said heaters having a parabolic reflector to illuminate an entire width of said strip by infrared radiation;
   c) a detection box disposed between said pair of quartz infrared heaters and disposed above said strip to detect a reflected portion of said infrared radiation reflected off said strip, said detection box including;
   d) an infrared sensor including an arsenide photovoltaic infrared diode sensitive to infrared wavelengths within a range from 1 to 3.5 microns and producing a first signal representative of an intensity of said reflected portion of said infrared radiation;
   e) an optical filter disposed between said infrared sensor and said strip limiting transmission of said reflected infrared light to a range from 2.7–2.9 microns;
   f) a lens disposed between said optical filter and said infrared sensor to focus said reflected light onto said sensor; and
   g) an amplifier receiving said first signal and producing therefrom an amplified voltage signal representative of said intensity of said reflected portion of said infrared radiation.

16. A non-invasive method of detecting water on a surface of a steel sheet coated in a continuous coating line to prevent the formation of water stains thereon, said method comprising the steps of:
   directing an infrared light having a wavelength substantially absorbed by water onto a selected surface area of the steel sheet;
   sensing a reflected portion of said infrared light from said selected surface area to determine an intensity thereof;
   determining the presence of water on said selected surface area by comparing said intensity to a predetermined value; and
   providing a condition whereby detected water is removed from the surface of the steel sheet before coiling to prevent the formation of water stains thereon.

17. The method of claim 16, further comprising the step of:
   filtering said infrared light to limit transmission thereof to within a pre-described range of wavelengths prior to said step of sensing.

18. The method of claim 17, wherein said pre-described range of wavelengths is within a range from 2.5 to 3.5 microns.

19. The method of claim 17, wherein said pre-described range of wavelengths is within a range from 2.7 to 2.9 microns.

20. The method of claim 19, wherein said step of filtering said infrared light filters said reflected portion of said infrared light.

21. The method of claim 17, wherein said pre-described range of wavelengths is within a range from 6 to 7 microns.

22. The method of claim 17, wherein said pre-described range of wavelengths is within a range from 1 to 2 microns.

23. The method of claim 17, in combination with a method of conveying said object in a rinse section of a steel treatment assembly, wherein said object is a strip of steel; said method further comprising the steps of:
   conveying said strip of steel along said rinse section between a drying stage area and a coiler of said rinse section; and
   said step of directing said infrared light and said step of sensing said reflected portion of said infrared light occurring at a location between said drying stage and said coiler proximate a roller supporting a turn in said conveyed strip.

24. The method claim 17, wherein said step of sensing said reflected portion of said infrared light includes the additional step of producing a first signal representative of said intensity of said reflected portion of said infrared light and amplifying and converting said first signal to a second voltage signal and said step of determining the presence of water on said selected includes the step of comparing said second voltage signal to a predetermined threshold value.

25. A method of non-invasively detecting water on a surface of a moving strip of metal conveyed along a rinse section of a manufacturing assembly, said method comprising the steps of:
   conveying said strip of metal along said rinse section between a drying stage area and a coiler of said rinse section;
   directing an infrared light having a wavelength substantially absorbed by water onto said strip;
   filtering said infrared light to limit transmission thereof to within a range of wavelengths from 2.7 to 2.9 microns;
   sensing a reflected portion of said infrared light reflected off said select strip to determine an intensity thereof, and producing a first signal representative of said intensity of said reflected portion of said infrared light;
   amplifying and converting said first signal to a second voltage signal; and
   determining the presence of water on said strip area by comparing said second voltage signal to a predetermined threshold value;
   wherein, said step of directing said infrared light and said step of sensing said reflected portion of said infrared light occurring at a location between said drying stage and said coiler proximate a roller supporting a turn in said conveyed strip of metal.

26. Apparatus for detecting the presence water on the surface of a continuous moving metal sheet to prevent the formation of water stains thereon, comprising:
   a) an energy source positioned to transmit radiant energy onto a surface target area of the continuous moving metal sheet, said radiant energy having a wavelength substantially absorbed by water;
   b) a sensor positioned to receive reflected radiant energy from said surface target area, said sensor generating an output signal indicative of an intensity difference between of said transmitted radiant energy and said reflected radiant energy, a predetermined difference indicating the presence of water; and
   c) a control device to initiate a condition whereby detected water may be removed from the surface of the continuous moving metal sheet to prevent the formation of water stains thereon.

27. The invention recited in claim 26, further comprising:
   a) a filter located between said reflected radiant energy and said sensor to limit to a selected wavelength the reflected radiant energy received by said sensor.

28. A method for detecting water on a surface of a metal sheet to prevent the formation of water stains thereon, comprising the steps of:

directing radiant energy having a wavelength substantially absorbed by water onto a surface target area of said metal sheet;

sensing a reflected radiant energy from said surface target area to determine an intensity thereof;

determining a presence of water on said surface target area by comparing said intensity to a predetermined value; and providing a control device to initiate a condition whereby detected water may be removed from the surface of the continuous moving metal sheet to prevent the formation of water stains thereon.

29. A non-invasive method of detecting water on a surface of a strip, said method comprising the steps of:

conveying said strip between a drying stage area and a coiler in a rinse section of a treatment line;

directing an infrared light having a wavelength substantially absorbed by water onto a selected area of the strip;

sensing a reflected portion of said infrared light reflected off said selected surface area to determine an intensity thereof; and determining the presence of water on said selected area by comparing said intensity to a predetermined value.

30. The method of claim 29 wherein said step directing said infrared light and said step of sensing said reflected portion of said infrared light occurs at a location between said drying stage and said coiler proximate a roller supporting a change in direction of the conveyed strip.

31. The method of claim 29, further comprising the step of:

filtering said infrared light to limit transmission thereof to within a pre-described range of wavelengths prior to said step of sensing.

32. The method of claim 29 wherein the strip is steel and the drying stage area and the coiler are located in the rinse section of a continuous coating line.

33. A non-invasive method of detecting water on a surface of an object, said method comprising the steps of:

rinsing said object;

drying said object;

directing an infrared light having a wavelength substantially absorbed by water onto a select area of said dried object;

sensing a reflected portion of said infrared light from said select area to determine an intensity thereof; and determining the presence of water on said selected area by comparing said intensity to a predetermined value.

34. The method of claim 33, further comprising the step of:

filtering said infrared light to limit transmission thereof to within a pre-described range of wavelengths prior to said step of sensing.

35. An apparatus for non-invasive detection of water on a continuous strip conveyed along a rinse section and drying section in a treatment line, said apparatus comprising:

a) an infrared light source positioned to transmit a generated infrared light of a predetermined intensity onto a selected surface area of the continuous strip, said generated infrared light having a wavelength substantially absorbed by water; and b) a sensor assembly having a sensor positioned to sense reflected infrared light reflected off said selected surface area, said assembly producing a signal representative of a second intensity of said reflected infrared light for comparison with said predetermined intensity to thereby detect a presence of water on said surface.

36. The invention according to claim 35, further comprising:

a) a filter located between said infrared light source and said sensor to limit an amount of said reflected infrared light detected by said sensor within a predetermined wavelength range.

37. The invention according to claim 35, wherein a) said infrared light source and said sensor assembly are positioned proximate a roller supporting a change in direction of said continuous strip conveyed along the rinse section and drying section of the treatment line.

38. The invention according to claim 35, wherein said sensor assembly includes a plurality of sensors, comprising:

a) a plurality of rotating polyhedral mirrors disposed between the continuous strip and said sensor assembly and each positioned to scan a portion of an entire width of said continuous strip and direct infrared light reflected off said selected surface area toward a corresponding one of said plurality of sensors thereby facilitating sensing of said entire width of said continuous strip.

39. The apparatus according to claim 35, said sensor assembly comprises an array of sensors, each of said sensors adapted to sense a width portion of the continuous strip, said array of sensors together sense reflected light across an entire width of the continuous strip.

40. The apparatus according to claim 35, wherein said light source comprises a pair of quartz infrared heaters disposed above the continuous strip and each having a parabolic reflector mounted there above to illuminate said select area by infrared radiation.

41. The invention according to claim 35, wherein the continuous strip is a continuous metal strip.

42. The invention according to claim 35, wherein the continuous strip is a continuous steel strip.

43. In a continuous treatment line that applies a coating to at least one surface of a moving metal strip, the improvement comprising: an infrared light source, a sensor, and a control device that communicate to illuminate and scan said at least one surface of the moving metal strip with infrared light at a wavelength substantially absorbed by water, and to initiate a condition whereby detected water is removed from said at least one surface to prevent the formation of water stains thereon.

* * * * *